US008761872B2

(12) United States Patent
Hinrichsen et al.

(10) Patent No.: US 8,761,872 B2
(45) Date of Patent: Jun. 24, 2014

(54) APPARATUS FOR STIMULATING AURICULAR POINTS ON THE HUMAN EAR

(75) Inventors: Uwe Hinrichsen, Boca Raton, FL (US); Jurgen Kruppa, Delray Beach, FL (US)

(73) Assignee: 16Max Corporation, Pompano Beach, FL (US)

( * ) Notice: Subject to any disclaimer, the term of this patent is extended or adjusted under 35 U.S.C. 154(b) by 366 days.

(21) Appl. No.: 12/751,371

(22) Filed: Mar. 31, 2010

(65) Prior Publication Data

US 2011/0093049 A1 Apr. 21, 2011

Related U.S. Application Data

(63) Continuation-in-part of application No. 12/719,343, filed on Mar. 8, 2010, now abandoned.

(60) Provisional application No. 61/252,338, filed on Oct. 16, 2009.

(51) Int. Cl.
*A61N 1/04* (2006.01)

(52) U.S. Cl.
USPC .............................................. 607/2; 607/149

(58) Field of Classification Search
USPC ........... 607/2, 40–42, 44–48, 50, 53–58, 115, 607/136, 139, 149
See application file for complete search history.

(56) References Cited

U.S. PATENT DOCUMENTS

| | | | | |
|---|---|---|---|---|
| 5,906,635 | A * | 5/1999 | Maniglia | 607/57 |
| 7,336,993 | B1 | 2/2008 | Szeles | |
| 7,822,479 | B2 * | 10/2010 | Stracener | 607/57 |
| 2005/0102006 | A1 * | 5/2005 | Whitehurst et al. | 607/46 |
| 2006/0004423 | A1 * | 1/2006 | Boveja et al. | 607/46 |
| 2006/0195160 | A1 * | 8/2006 | Blamey et al. | 607/57 |
| 2006/0247735 | A1 * | 11/2006 | Honert | 607/57 |
| 2007/0179566 | A1 * | 8/2007 | Gantz et al. | 607/57 |
| 2008/0097549 | A1 * | 4/2008 | Colbaugh et al. | 607/55 |
| 2008/0154339 | A1 * | 6/2008 | Carter | 607/57 |

OTHER PUBLICATIONS

Instructions for Use—P-Stim; Biegler GmbH, Mauerbach, Austria; Date of Issue: Jan. 2007.

* cited by examiner

*Primary Examiner* — Allen Porter, Jr.
(74) *Attorney, Agent, or Firm* — Scott D. Smiley; Yongae Jun; Mark C. Johnson

(57) ABSTRACT

An apparatus for stimulating auricular points on the human ear is provided using low voltage pulses that are generated and delivered by portions of the apparatus that may be readily removed from the neck and ear, and then easily replaced by the patient to continue therapy.

25 Claims, 4 Drawing Sheets

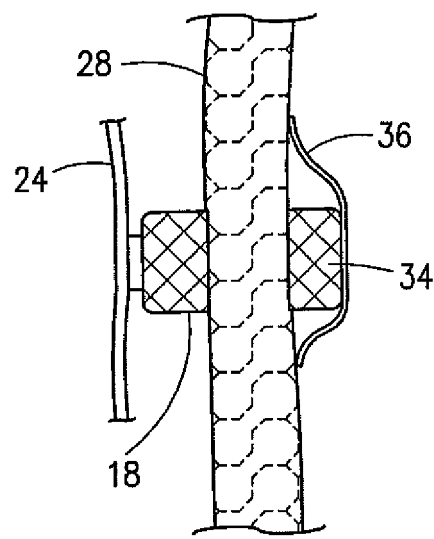
FIG. 3
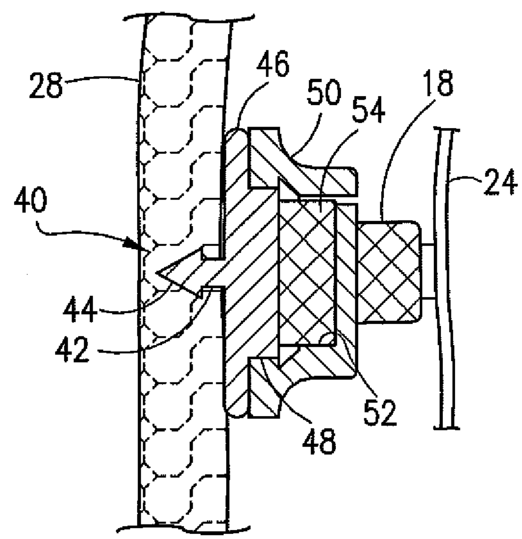
FIG. 4
FIG. 5
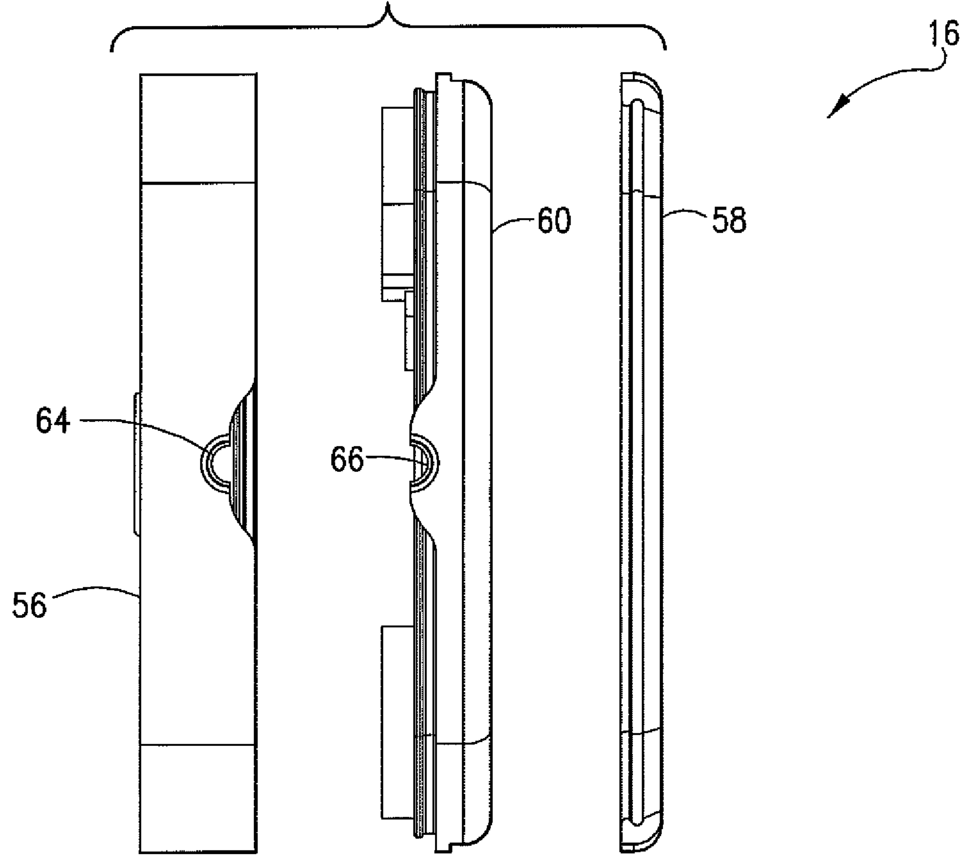

FIG. 6
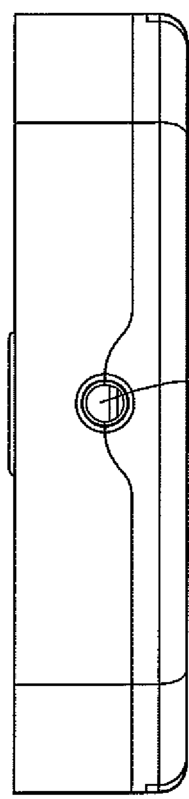
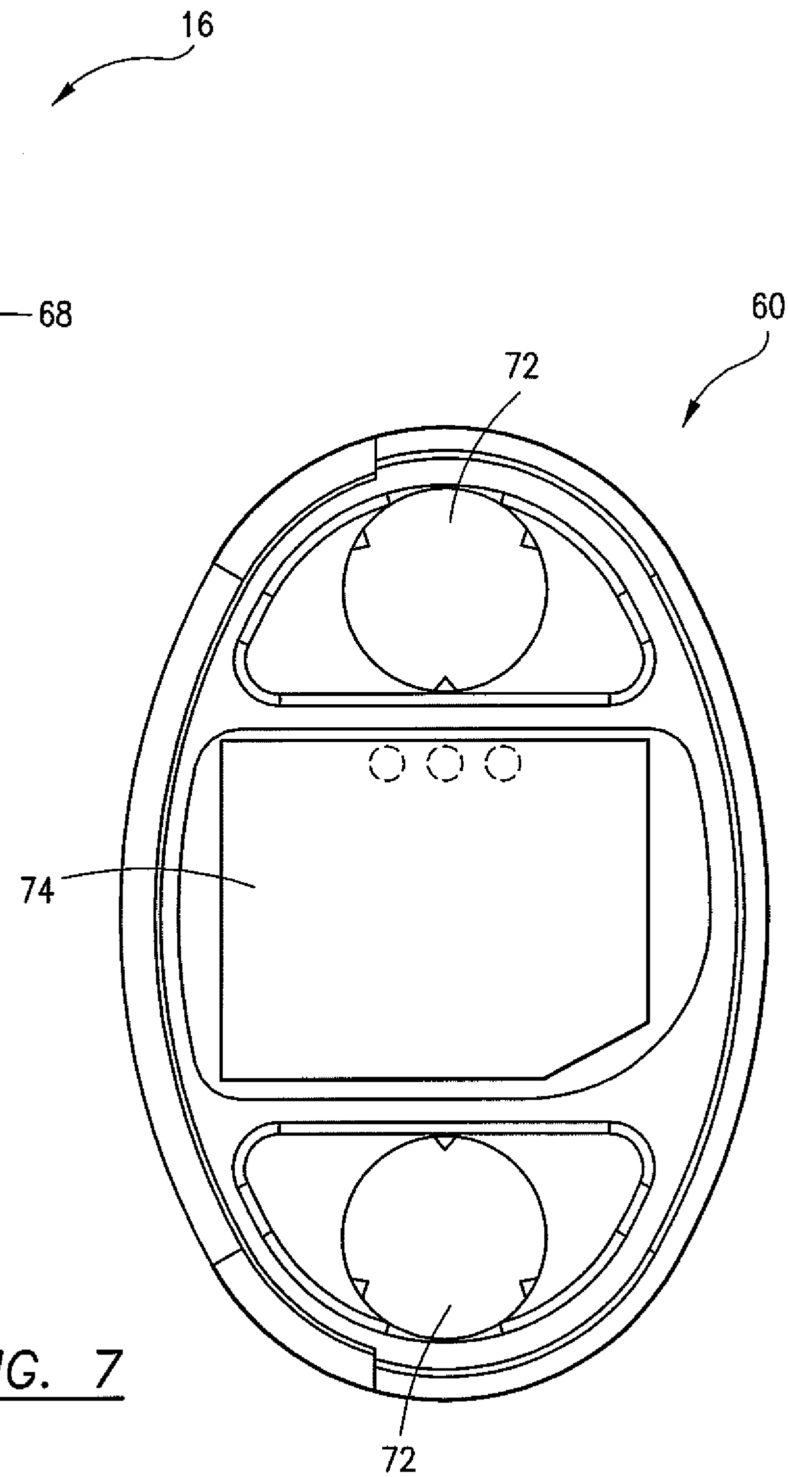
FIG. 7

APPARATUS FOR STIMULATING AURICULAR POINTS ON THE HUMAN EAR

CROSS-REFERENCE TO RELATED APPLICATIONS

This application is a continuation-in-part of U.S. patent application Ser. No. 12/719,343 filed Mar. 8, 2010 and claims the benefit of U.S. Provisional Application Ser. No. 61/252,338 filed Oct. 16, 2009 under 35 U.S.C. §119(e) for all commonly disclosed subject matter which is expressly incorporated herein by reference in its entirety to form part of the present disclosure.

FIELD OF THE INVENTION

This invention relates to an apparatus for stimulating auricular points on the human ear, and, more particularly, to an apparatus having a number of treatment devices coupled to an electronic circuit carried by a housing removably attached to the neck near the ear via a mounting pad wherein the treatment devices may be retained at selected auricular points on the ear, temporarily removed with or without the housing, and then later reattached.

BACKGROUND OF THE INVENTION

Auricular therapy is based on the concept that nerves in the external ear connect to parts of the brain which have reflex connections to the body. According to auricular therapy, each area of the ear is related to a different anatomical portion of the body. A large number of sites on the ear have been identified which exhibit changes in tenderness and altered blood circulation in response to the presence of disease, injury or other problems in corresponding parts of the body. Auricular therapy has been utilized to treat conditions in distant parts of the body by stimulating the particular point(s) on the ear corresponding to the injured or diseased body part using acupuncture, massage or electric pulses. The most common health conditions treated by auricular therapy including the control of chronic pain, detoxification from addictions, relief from nausea, high blood pressure, arthritis, asthma, indigestion, migraines, urinary problems and nervous disorders. Clinical studies on humans have shown that stimulation of auricular points on the ear appear to cause the systemic release of endogenous morphine or “endorphins” which are particularly effective in the control of chronic pain.

SUMMARY OF THE INVENTION

This invention is directed to an apparatus for stimulating auricular points on the human ear using electric pulses that are generated and delivered by portions of the apparatus that may be readily removed from the head and ear, and then easily replaced by the patient to continue therapy.

In one presently preferred embodiment of this invention, a mounting pad having a reference electrode is attached to the neck near the back of the ear. The mounting pad supports a housing that contains an electronic circuit coupled to the reference electrode and to a wire connected to a number of treatment devices. The circuit is effective to deliver electrical pulses to the treatment devices at a voltage level that may be adjusted. Each treatment device may be held in position at a selected auricular point on the ear by either a backing magnet, located on the side of the ear opposite the treatment device, or a needle assembly having a needle inserted into the ear.

An important advantage of the apparatus of this invention is that the housing which contains the electronic circuit, and the treatment devices, may be removed by the patient while the mounting pad and the backing magnet or needle assembly remain in place. This allows the patient to shower, wash his or her hair etc. without damaging the apparatus. Thereafter, the housing may be reattached to the mounting pad and the treatment devices placed back in position, without the assistance of a physician, to resume treatment of the selected auricular area(s). Additionally, unlike prior art devices, the magnitude of the voltage output from the electronic circuit may be adjusted depending upon whether the treatment device is held in place on the ear by a backing magnet or by a needle inserted into the ear.

BRIEF DESCRIPTION OF THE DRAWINGS

The structure, operation and advantages of the presently preferred embodiment of this invention will become further apparent upon consideration of the following description, taken in conjunction with the accompanying drawings, wherein:

FIG. 3 is a view in partial cross section depicting the side of an ear with a treatment device held in place on the ear by a backing magnet;

FIG. 4 is a view in partial cross section illustrating the side of an ear with a treatment device held in place on the ear by a needle assembly;

FIG. 5 is an exploded, side view of the components forming the circuit housing of this invention;

FIG. 6 is an assembled, side view of the circuit housing depicting the port for connection of the wire coupled to the treatment devices;

FIG. 7 is a plan view of the middle plate portion of the circuit housing schematically depicting a printed circuit board in place in the center area thereof.

DETAILED DESCRIPTION OF THE INVENTION

Figure 1:
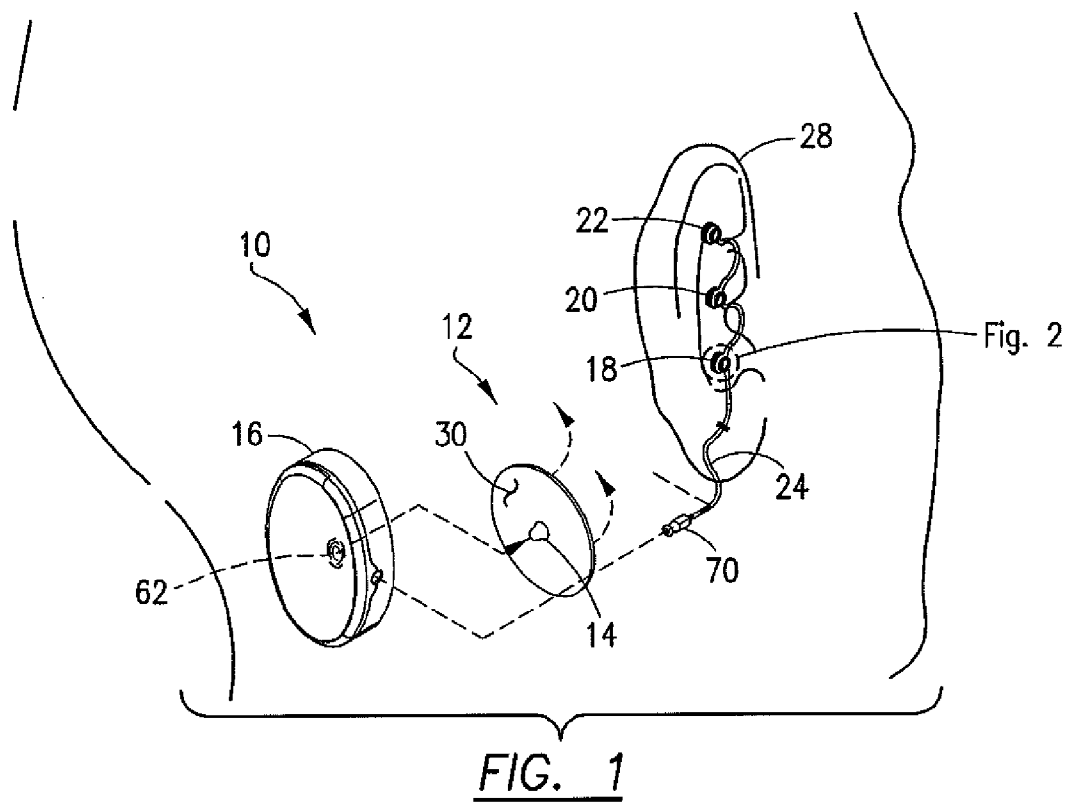
FIG. 1 is schematic, side view of a human head depicting the location at which the mounting pad and circuit housing may be attached to the human body, and the positioning of treatment devices at selected auricular points on an ear.
Figure 2:
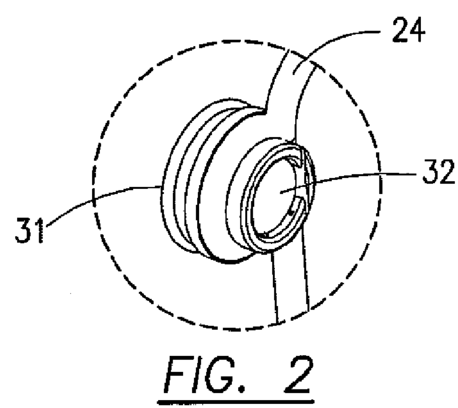
FIG. 2 is an enlarged view of one of the treatment devices shown in FIG. 1.

Referring initially to FIGS. 1 and 2, the auricular device 10 of this invention comprises a mounting pad 12 having a ground or reference electrode 14, a circuit housing 16 and treatment devices 18, 20 and 22 each connected by a common wire 24 to the housing 16. The device 10 is schematically depicted with the housing 16 attached to the neck of a patient, just below his or her ear 28, with each of the treatment devices 18, 20 and 22 positioned at a selected auricular point on the exterior surface of the skin of the ear 28. Each of the components of the auricular device 10 is described separately below, followed by a discussion of the operation of the device 10.

The mounting pad 12 may be a standard electrode of the type employed in electrocardiogram machines including a circular-shaped section 30 of flexible plastic which mounts the reference electrode 14. The plastic section 30 has adhesive on one side that may be placed against the skin of the patient, preferably on the neck just below the ear 28 as noted above. As discussed in more detail below, the mounting pad 12 functions to support the housing 16 and its reference electrode 14 provides a ground connection for electronic circuit located within the housing 16.

As best seen in FIG. 2, each of the treatment devices 18-20 comprises a casing 31 within which a magnet 32 or metallic element having magnetic properties is mounted. The term "metallic element" as used herein refers to an alloy containing a magnetic metal such as iron, nickel or cobalt which is attracted to a magnet. The wire 24 is coupled to the casing 31 so that it electrically contacts the magnet 32, for purposes discussed in detail below.

As noted above, each of the treatment devices 18-22 is positioned at a selected auricular point on the ear 28 so that they may deliver a pulsed voltage for treatment purposes. With reference to FIGS. 3 and 4, two methods are contemplated in this invention for positioning the treatment devices 18-22. In the embodiment depicted in FIG. 3, a permanent, backing magnet 34 is placed on the side of the ear 28 opposite one of the treatment devices 18-22, e.g. the treatment device 18 as illustrated in FIG. 3. Preferably, the backing magnet 34 is held in place on the ear by a strip 36 of medical tape, such as "Medipore" surgical tape commercially available from the Minnesota Mining and Manufacturing Company of St. Paul, Minn. The metallic element or magnet 32 of the treatment device 18 is held in place on the ear 28 by the magnetic field produced by the permanent, backing magnet 34 located on the opposite side of the ear 28.

Alternatively, a needle assembly 38 is employed to retain the treatment devices 18-22 in place. As shown in FIG. 4, each needle assembly 38 includes a needle 40 having a shaft 42 with a point 44 and one end and a plate 46 connected at its opposite end. The plate 46 has a seat 48 that receives a cover 50 forming a cavity 52 within which a permanent magnet 54 is mounted. The needle 40 is extended into the ear 28 so that the plate 46 rests against one side of the ear 28. The size of needle 40 and its depth of penetration into the ear 28 are exaggerated in FIG. 4 for purposes of illustration. If desired, a strip of surgical tape (not shown) may be placed along the plate 46 to help hold the needle 40 in place. The cover 50 encloses the end of the plate 46 and permanent magnet 54, but it is relatively thin and allows the magnetic field produced by the permanent magnet 54 to attract the treatment device 18 which rests against the outside surface of the cover 50.

It is contemplated that the backing magnet 34 and needle assembly 38 may be positioned at the appropriate auricular point on the ear 28 by a physician or other health care professional. Both are intended to remain in position during the useful life of the device 10 of this invention while allowing the patient to shower, wash his or her hair etc. without damaging either. As discussed below, the treatment device 18 may be readily removed from the opposite side of the ear (FIG. 3) or from the cover 50 of needle assembly 38 (FIG. 4) when the device 10 is not operating or when the patient wishes to shower etc.

Referring now to FIGS. 5-7, the circuit housing 16 of this invention is shown in more detail. In one presently preferred embodiment, the housing 16 comprises a base 56, a cap 58 and a middle plate 60 connected between the base 56 and cap 58. The base 56 is formed with a central bore 62 which engages the reference electrode 14 of the mounting pad 12, as schematically shown in FIG. 1, and a recess 64 in its side edge. The middle plate 60 has a mating recess 66 along its side edge, which, when the base 56 and middle plate 60 are connected, forms a port 68 with the recess 64 in base 56. The port 68 connects to a coupler 70 at the end of wire 24, as seen in FIG. 1, or to a serial interface described below in connection with a discussion of the electronic circuit of device 10. As best seen in FIG. 7, the middle plate 60 is formed with an opening 72 at either end, each of which mounts a battery (not shown). A central area of the middle plate 60 mounts a printed circuit board 74 which carries the electronic circuit of device 10 schematically illustrated in FIG. 8. The base 56 and cap 58 capture and support the middle plate 60 between them, as seen in FIG. 6.

Figure 8:
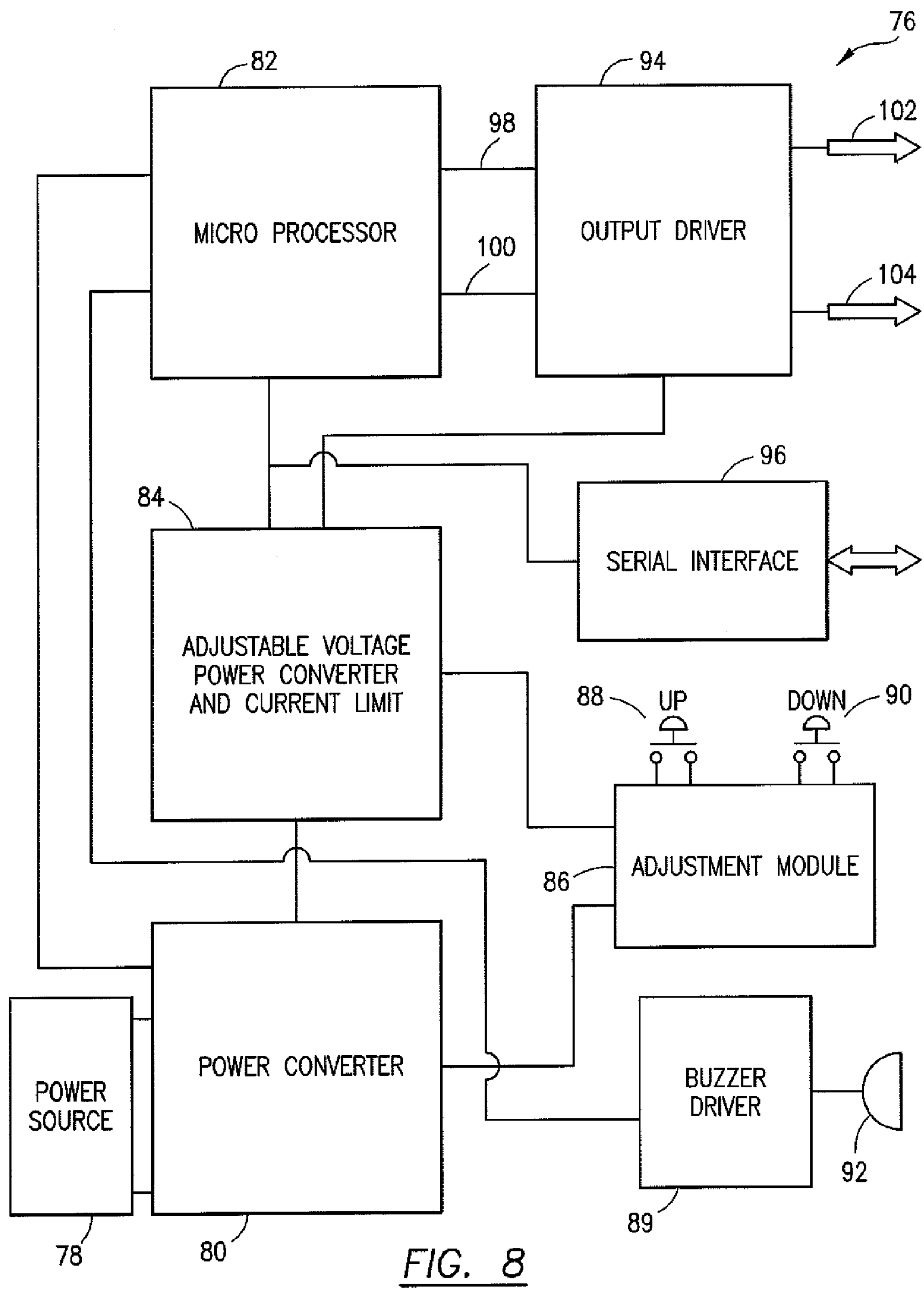
FIG. 8 is a schematic, block diagram of the electronic circuit employed in the device herein.

A schematic, block diagram of the electronic circuit 76 employed in the auricular device 10 of this invention is shown in FIG. 8 wherein each block is representative of a circuit element. The block identified with the reference 78 is denoted as a "power source," which may comprise one, two or more batteries. The power source 78 is coupled to a power converter 80, which, in turn, is coupled to a microprocessor 82, to an adjustable voltage power converter and current limit 84, and, to an adjustment module 86. The adjustment module 86, having schematically depicted "up" and "down" controls 88, 90, respectively, is coupled to the power convertor 80. A buzzer driver 89 is coupled to the microprocessor 82 and to a buzzer 92. Both the adjustable voltage power convertor and current limit 84 and the microprocessor 82 are coupled to an output driver 94, and the adjustable voltage power convertor and current limit 84 is coupled to the adjustment module 86. The output driver 94, in turn, is coupled to the wire 24 and to the reference electrode 14 of the mounting pad 12 which functions as a ground or reference for the electronic circuit 76. A serial interface 96 may be coupled to the microprocessor 82, as discussed below.

The auricular device 10 is operated as follows. Initially, auricular points on the outer part of the ear 28 are identified depending upon the symptoms or other conditions of a particular patient. The identification of auricular points and/or their correlation with different health conditions forms no part of this invention and is therefore not discussed herein. However, once such points are identified by a health care professional, the device 10 of this invention is employed to deliver a pulsed voltage to such points.

As noted above, the mounting pad 12 is adhered to the neck of a patient, preferably in the area beneath the ear 28, with the reference electrode 14 exposed. The housing 16 may be removably attached to the mounting pad 12 by insertion of the reference electrode 14 though the central bore 62 in the base 56 of the housing 16. The output driver 94 of electronic circuit 76 is connected to each of the treatment devices 18, 20 and 22 by the wire 24. As discussed above, each treatment device 18-20 is held in position at one of the selected auricular points on the ear 28 either by a backing magnet 34 or a needle assembly 38.

One important aspect of this invention is the removable nature of both the housing 16 and the treatment devices 18-22 from their positions on the patient. Water from bathing or other sources can damage the electronic circuit 76 and treatment devices 18-22. Before taking a shower, for example, the housing 16 may be removed from the mounting pad 12 and the treatment devices 18-22 may be disengaged from the backing magnets 34 or needle assemblies 38. The wire 24 may remain attached to the housing 16 or unplugged at the connection of the coupler 70 at one end of wire 24 to the port 62 in housing 16. While the backing magnets 34 and needle assemblies 38 would remain in place, they are not harmed in any way by contact with water. Once the patient has dried from a shower or other exposure to water, he or she may reinsert the housing 16 onto the mounting pad 12 and reposition the treatment devices 18-22 relative to the backing magnets 34 or needle assemblies 38, as described above, in order to continue treatment without the assistance of a physician or other health car professional.

The circuit 76 of this invention functions to produce a pulsed, low voltage output to stimulate the auricular points at which the treatment devices 18-22 are located. Power is supplied from the power source 78 via the power convertor 80 to the microprocessor 82 which has a self-contained circuit (not shown) that generates an output pulse train in the form of a square wave having alternately a plus and minus component represented by the lines 98 and 100 from microprocessor 82 connected to the output driver 94, and lines 102 and 104 output from the output driver 94. One of the lines 102, 104 is connected to the wire 24, and the other of the lines 102, 104 is coupled to the ground electrode 14 of mounting pad 12 to act as a reference or ground. The magnitude of the voltage output from the output driver 94 is controlled by the adjustable voltage power convertor and current limit 84 and the adjustment module 86. In the presently preferred embodiment, a manually operated dial or switches associated with the adjustment module 86, which are schematically illustrated in FIG. 8 as the "up" control 88 and "down" control 90, may be operated to adjust the voltage up or down depending upon whether the treatment devices 18-22 are located on the ear 28 using a backing magnet 34 or a needle assembly 38. It has been found that less voltage is required for effective treatment, and also desired for comfort purposes, when using a needle assembly 38 to retain a treatment device 18-22 in place compared to a backing magnet 34. Preferably, when using a needle assembly 38 the voltage output to the treatment devices 18-22 is in the range of about 4 volts to 6 volts, whereas the voltage output to treatment devices 18-22 when using a backing magnet 34 is in the range of about 9 volts to 24 volts.

The circuit 76 is designed to operate for a one to three hour treatment cycle, automatically shut down for a similar period of time and then start again for another treatment cycle. The buzzer driver 89 and buzzer 92 are provided to notify the patient of these events. The buzzer driver 89 consists of a timed oscillator-driven piezoelectric element designed for minimal power consumption. The microprocessor 82 controls the buzzer driver 89 such that it is activated at the beginning of each treatment cycle to cause the buzzer 92 to produce a number of short sound bursts, e.g. three, for example. This alerts the patient to the onset of a treatment cycle. The removable nature of the components of this invention allows the patient, if desired, to detach the housing 16 from the mounting pad 12 and the treatment devices 18-22 from the ear 28 during periods in between treatment cycles for enhanced comfort. The housing 16 and treatment devices 18-22 may be repositioned when the patient is alerted by the buzzer 92 to the start of another treatment cycle, in the manner described above.

The embodiment of the invention discussed above provides the patient with the ability to adjust the voltage output to the treatment devices 18-22 by manipulation of the "up" and "down" controls 88, 90. It should be understood that such voltage levels could be set at the factory, allowing for no adjustment by the patient or healthcare professional, in which case the housing 16 and treatment devices 18-22 would be intended for use only with backing magnets 34 or with needle assemblies 38 depending on the magnitude of the set voltage as discussed above.

It is contemplated that in some instances the healthcare professional may wish to make changes to the voltage output to the treatment devices 18-22, such as the pulse frequency, the pulse width, the provision of sequential pulses, the output of more than one pulse at a time and the like. These variations in the operation of device 10 are made possible using the serial interface 96. The term "serial interface" as used herein refers to device that may be coupled to the electronic circuit 76 via port 62, and to a computer or the like having software capable of being downloaded to the microprocessor 82 of the circuit 76. Once downloaded to the microprocessor 82, such software would control the voltage output to the treatment devices 18-22, as desired.

While the invention has been described with reference to a preferred embodiment, it should be understood by those skilled in the art that various changes may be made and equivalents substituted for elements thereof without departing from the scope of the invention. In addition, many modifications may be made to adapt a particular situation or material to the teachings of the invention without departing from the essential scope thereof.

For example, three treatment devices 18, 20 and 22 are depicted in the drawings but it should be understood that a different number of such treatment devices may be employed, as desired.

Therefore, it is intended that the invention not be limited to the particular embodiment disclosed as the best mode contemplated for carrying out this invention, but that the invention will include all embodiments falling within the scope of the appended claims.

What is claimed is:

1. An apparatus for stimulating one or more auricular points on an external human ear, comprising:

a mounting pad adapted to removably attach to a patient, said mounting pad having a reference electrode;

a housing having an electronic circuit, said housing being releasably mounted to said mounting pad so that said electronic circuit is coupled to said reference electrode;

at least one auricular treatment device coupled to said electronic circuit, said at least one auricular treatment device including an element having magnetic properties;

at least one support adapted to be attached at a selected auricular point on the external ear, said at least one support magnetically attracting said element of said at least one auricular treatment device to retain said at least one auricular treatment device on the external ear; and said electronic circuit being effective to produce a pulsed voltage output which is transmitted to said at least one auricular treatment device to stimulate said selected auricular point on the external ear.

2. The apparatus of claim 1 in which said element of said at least one auricular treatment device is a permanent magnet.

3. The apparatus of claim 1 in which said element of said at least one auricular treatment device contains a magnetic metal.

4. The apparatus of claim 1 in which said at least one support is a backing magnet.

5. The apparatus of claim 4 in which said backing magnet is adapted to be secured to one side of the external ear at a selected auricular point by a strip of tape.

6. The apparatus of claim 4 in which said electronic circuit produces a first output voltage when said at least one support is said backing magnet.

7. The apparatus of claim 4 in which said at least one support is a needle assembly having a needle adapted for extending into the external ear at said selected auricular point, a cover formed with a cavity which is connected to said needle and a permanent magnet located within said cover.

8. The apparatus of claim 7 in which said electronic circuit produces a second output voltage when said at least one support is a needle assembly, said second voltage being less than said first voltage.

9. The apparatus of claim 1 in which said housing and said at least one auricular treatment device are adapted to be detached from said mounting pad and disengaged from said at least one support, respectively, while said mounting pad and said at least one support remain in place.

10. The apparatus of claim 1 in which said at least one auricular treatment device comprises a number of auricular treatment devices, and said at least one support comprises a number of supports each adapted for positioning one of said auricular treatment devices at a different auricular point on the external human ear.

11. The apparatus of claim 1 in which said electronic circuit is effective to adjust the magnitude of the pulsed output voltage transmitted to said at least one auricular treatment device.

12. The apparatus of claim 11 in which said pulsed output voltage is in the range of about 4 volts to about 24 volts.

13. The apparatus of claim 1 in which said electronic circuit includes a microprocessor and a serial interface, said serial interface being effective to download software to said microprocessor which causes said microprocessor to alter the pulsed voltage output to said at least one auricular treatment device.

14. An apparatus for stimulating auricular points on an external human ear, comprising:

a mounting pad adapted to removably attach to a patient, said mounting pad having a reference electrode;

a housing having an electronic circuit, said housing being releasably mounted to said mounting pad so that said electronic circuit is coupled to said reference electrode;

at least one auricular treatment device coupled to said electronic circuit, said at least one auricular treatment device including an element having magnetic properties;

at least one backing magnet adapted to be attached to one side of the external ear at a selected auricular point, said at least one backing magnet being effective to provide a magnetic field which attracts said element of said at least one auricular treatment device and releasably retain said at least one auricular treatment device on the opposite side of the external ear in alignment with said backing magnet; and said electronic circuit being effective to produce a pulsed voltage output which is transmitted to said at least one auricular treatment device to stimulate said selected auricular point on the external ear.

15. The apparatus of claim 14 in which said electronic circuit produces a pulsed voltage output in the range of about 9 volts to about 24 volts.

16. The apparatus of claim 14 in which said housing and said at least one auricular treatment device are adapted to be detached from said mounting pad and disengaged from said at least one backing magnet while said mounting pad and said at least one backing magnet remain in place.

17. The apparatus of claim 14 in which said at least one auricular treatment device comprises a number of auricular treatment devices, and said at least one backing magnet comprises a number backing magnets each adapted for positioning one of said auricular treatment devices at a different auricular point on the external human ear.

18. The apparatus of claim 14 in which said electronic circuit is effective to adjust the magnitude of the pulsed output voltage transmitted to said at least one auricular treatment device.

19. The apparatus of claim 14 in which said electronic circuit includes a microprocessor and a serial interface, said serial interface being effective to download software to said microprocessor which causes said microprocessor to alter the pulsed voltage output to said at least one auricular treatment device.

20. An apparatus for stimulating one or more auricular points of an external human ear, comprising:

a mounting pad adapted to removably attach to a patient, said mounting pad having a reference electrode;

a housing having an electronic circuit, said housing being releasably mounted to said mounting pad so that said electronic circuit is coupled to said reference electrode;

at least one auricular treatment device coupled to said electronic circuit, said at least one auricular treatment device including an element having magnetic properties;

at least one needle assembly coupled to said electronic circuit, said at least one needle assembly having a needle adapted for extending into the external ear at a selected auricular point, a cover formed with a cavity which is adapted to be connected to the external ear and a permanent magnet located within said cavity, said permanent magnet of said at least one needle assembly being effective to produce a magnetic field which attracts said element of said at least one auricular treatment device to releasably retain said at least one auricular treatment device against said cover;

said electronic circuit being effective to produce a pulsed voltage output which is transmitted to said at least one auricular treatment device to stimulate said selected auricular point on the external ear.

21. The apparatus of claim 20 in which said electronic circuit produces a pulsed voltage output in the range of about 4 volts to about 8 volts.

22. The apparatus of claim 20 in which said housing and said at least one auricular treatment device may be detached from said mounting pad and disengaged from said at least one needle assembly while said mounting pad and said at least one needle assembly remain in place.

23. The apparatus of claim 20 in which said at least one auricular treatment device comprises a number of auricular treatment devices, and said at least one needle assembly comprises a number of needle assemblies each adapted for positioning one of said auricular treatment devices at a different auricular point on the external human ear.

24. The apparatus of claim 20 in which said electronic circuit is effective to adjust the magnitude of the pulsed output voltage transmitted to said at least one auricular treatment device.

25. The apparatus of claim 20 in which said electronic circuit includes a microprocessor and a serial interface, said serial interface being effective to download software to said microprocessor which causes said microprocessor to alter the pulsed voltage output to said at least one auricular treatment device.

* * * * *